United States Patent
Yang

(10) Patent No.: US 9,415,394 B2
(45) Date of Patent: Aug. 16, 2016

(54) MICROFLUIDIC CHIP WITH FLOW-GUIDING BODY AND APPLICATIONS THEREOF

(71) Applicant: BEIJING BOHUI INNOVATION TECHNOLOGY CO., LTD., Beijing (CN)

(72) Inventor: Qi Yang, Beijing (CN)

(73) Assignee: BEIJING BOHUI INNOVATION TECHNOLOGY CO., LTD., Beijing (CN)

( * ) Notice: Subject to any disclaimer, the term of this patent is extended or adjusted under 35 U.S.C. 154(b) by 0 days.

(21) Appl. No.: 14/396,630

(22) PCT Filed: Sep. 20, 2012

(86) PCT No.: PCT/CN2012/081673
§ 371 (c)(1),
(2) Date: Oct. 23, 2014

(87) PCT Pub. No.: WO2013/159484
PCT Pub. Date: Oct. 31, 2013

(65) Prior Publication Data
US 2015/0098864 A1    Apr. 9, 2015

(30) Foreign Application Priority Data

Apr. 23, 2012   (CN) .......................... 2012 1 0121023

(51) Int. Cl.
| | | |
|---|---|---|
| *B01L 3/00* | (2006.01) | |
| *C12M 1/40* | (2006.01) | |
| *G01N 33/00* | (2006.01) | |
| *G01N 33/53* | (2006.01) | |
| *G01N 27/447* | (2006.01) | |

(52) U.S. Cl.
CPC .......... *B01L 3/502746* (2013.01); *B01L 3/5025* (2013.01); *B01L 2200/0647* (2013.01); *B01L 2200/10* (2013.01); *B01L 2300/0861* (2013.01); *B01L 2300/0867* (2013.01); *B01L 2400/049* (2013.01); *B01L 2400/084* (2013.01); *B01L 2400/086* (2013.01); *B01L 2400/088* (2013.01); *G01N 27/44791* (2013.01)

(58) Field of Classification Search
CPC ................ B01L 2200/0647; B01L 2300/0861; B01L 2300/0867; B01L 2400/049; B01L 2400/084; B01L 3/5025; B01L 3/502746
See application file for complete search history.

(56) References Cited

U.S. PATENT DOCUMENTS

| | | | | |
|---|---|---|---|---|
| 5,098,845 | A * | 3/1992 | Babson ................. | B01L 3/5021 422/69 |
| 6,168,948 | B1 * | 1/2001 | Anderson ........... | B01F 11/0266 366/DIG. 3 |
| 2008/0206757 | A1 * | 8/2008 | Lin ..................... | G01N 33/5094 435/6.14 |
| 2009/0071833 | A1 * | 3/2009 | Gorfinkel .......... | B01L 3/502715 204/601 |
| 2009/0246082 | A1 * | 10/2009 | Saiki ................ | G01N 35/00069 422/72 |
| 2010/0187452 | A1 | 7/2010 | Mukaddam et al. | |

FOREIGN PATENT DOCUMENTS

| | | |
|---|---|---|
| CN | 101495236 A | 7/2009 |
| CN | 101643701 A | 2/2010 |
| CN | 102671726 A | 9/2012 |

* cited by examiner

*Primary Examiner* — Jennifer Wecker
(74) *Attorney, Agent, or Firm* — Morriss O'Bryant Compagni, PC

(57) ABSTRACT

A microfluidic chip (100) with a flow-guiding body (111) and the applications thereof in biochemistry, immunology, and molecule detection. The flow-guiding body (111) is disposed in a solution tank (101) of the microfluidic chip (100), the surface of the flow-guiding body (111) is enclosed by the antigen or antibody, and the gap between the flow-guiding body (111) and a wall (105) of the solution tank is 0 mm to 1.5 mm.

14 Claims, 6 Drawing Sheets

MICROFLUIDIC CHIP WITH FLOW-GUIDING BODY AND APPLICATIONS THEREOF

CROSS-REFERENCE TO RELATED APPLICATIONS

This application is a national phase entry under 35 U.S.C. §371 of PCT/CN2012/081673 filed on Sep. 20, 2012, which claims priority to Chinese Patent Application No. 201210121023.9 filed on Apr. 23, 2012, the entirety of each of which is incorporated by this reference.

TECHNICAL FIELD

The present application relates to the field of fluid control and detection in microscale, in particular, to a polymeric microfluidic chip with a flow-guiding body and applications thereof.

BACKGROUND

Fluid technology is a technology that detects and manipulates micro-volume fluid, as well as a method applying to structure analysis and control of a biological and chemical fluid system. The applications that microfluidic technology has realized and the potential applications include disease diagnosis, life science research, and biology and/or chemistry sensor development.

Polymeric microfluidic structure includes a substrate and diaphragms. In the structure of polymeric microfluidic, there may be various structures on the substrates, e.g. microfluidic channels or paths, through-holes, as well as various vessels. The combination of the substrate and the diaphragms may constitute a valve structure. The diaphragm will be deformed by being applied by force, thereby actuating the liquid to flow by the valve, hence forming a pump structure. The pump structure is coupled to the valve structure by external power and thus as a driving device for the liquid flowed within the microfluidic chip. According to the application requirements, the microfluidic chip is individually designed so as to realize efficient sample detection. "Microfluidic-controlled chip" is a microfluidic chip employing certain control manner. The polymeric microfluid is made of organic polymer, including rigid polymethylmethacrylate (PMMA), acrylonitrile-butadiene-styrene (ABS) and polystyrene (PS) etc.

The polymeric microfluidic structure characterizes in "micro", that is, micro overall structure, micro amount of used sample, micro used reagent volume, and micro fluid flow on the chip. Therefore, in order to obtain the precision and stability of the application target, it requires the high precision of the microfluidic control.

At present, the main problem of the microfluidic chip in the application is that the residual droplet will occur and adhere to the inner wall of the vessel during the outflow of the liquid from the vessel. Such residual, though small in amount, will produce a relative residual amount ratio to the microfluid which cannot be neglected. The residual liquid is the main factor that hinders the application of polymeric Microfluid.

As to the existing polymeric microfluidic chip with its vessel 101 shown in FIG. 3, after the solution is pumped out from the vessel, some adherent droplets will be left on the inner wall of the vessel, even though the inner wall of the vessel adopts the shape of an arc angle. Residual liquid will affect the detection result since it will produce error due to the decrease of the solution amount. In addition, when the vessel is reused, and other solution will be pumped into the vessel, resulting in contamination and thus affecting the normal reaction.

SUMMARY

To solve the problem in the existing microfluidic chip, an object of the present invention is to provide a micro-fluidic chip with a flow-guiding body.

The technical solution to achieve the object of the present invention is as follows:

A microfluidic chip with a flow-guiding body, wherein the flow-guiding body is disposed in a solution tank of the microfluidic chip, and a gap between the flow-guiding body and a wall of the solution tank is 0-1.5 mm.

Wherein, the shape of the flow-guiding body is varied depending on the shape of the solution tank, being sphere, oblate spheroid, polyhedron or irregular geometry. When the solution tank is of irregular shape, the flow-guiding body may be of irregular shape.

Wherein, the gap between the flow-guiding body and the wall of the solution tank depends on the viscosity of the solution (measured at room temperature), where the viscosity of the solution is 0.6-1.2 mPa·s, the gap is 0-0.9 mm, and where the viscosity of the solution is 1.2-6.0 mPa·s, the gap is 0.9-1.5 mm.

Wherein, the silicification is performed on the surface of the flow-guiding body. Silicification treatment adopts the conventional methods for performing the treatment of plastic components, for example, taking a silane solution as silicide liquid, immersing the flow-guiding body, and then performing drying.

Wherein, an antigen or antibody is coated on a surface of the flow-guiding body.

Wherein, a stopper is disposed over the flow-guiding body and the stopper is fastened to the wall of the solution tank. When the specific gravity of the sphere is lower than that of the liquid, the range of floating and moving is limited so that the flow-guiding body is fully immersed into the solution.

The microfluidic chip provided by the present application comprises the following six solution tanks: a sample tank, a dilution liquid tank, a marking liquid tank, a dissociation liquid tank, a washing liquid tank and an effluent liquid tank, each tank with a substrate through-hole provided at the bottom; wherein, a sample tank valve and a sample through-hole are provided in the sample tank, a dilution liquid tank valve and a dilution liquid through-hole are provided in the dilution liquid tank, a marking liquid valve and a marking liquid through-hole are provided in the marking liquid tank, a dissociation liquid tank valve and a dissociation liquid through-hole are provided in the dissociation liquid tank, a washing liquid valve and a washing liquid through hole are provided in the washing liquid tank, and an effluent liquid valve and an effluent liquid through-hole are provided in the effluent liquid tank; each valve is connected to a main valve via channels.

The sample tank valve, the main valve, the dilution liquid tank valve as well as the through-holes and channels constitute a two-way sample dilution pump between the sample tank and the dilution liquid tank.

The sample tank valve, the main valve, the washing liquid valve as well as the through-holes and channels constitute a one-way sample washing pump between the sample tank and the washing liquid tank.

The sample tank valve, the main valve, the effluent liquid valve as well as the through-holes and channels constitute a one-way sample effluent liquid pump between the sample tank and the effluent liquid tank.

The sample tank valve, the main valve, the marking liquid valve and the channels constitute a two-way sample marking pump between the sample tank and the marking liquid tank.

The sample tank valve, the main valve, the dissociation liquid tank valve and the channels constitute a two-way sample dissociation reinforce pump between the sample tank and the dissociation reinforce liquid tank.

The present application provides application of the microfluidic chip according to the present application in biochemistry, immunology, and molecule detection.

The advantageous effects of the present application are as follows:

It can reduce the residual of the discharge liquid. During the discharge of the solution each time, when the solution is discharged from the through-hole, negative pressure is generated by the pump, and the airflow is thus generated. In the presence of a flow-guiding body, a gap is formed between the flow-guiding body and the vessel, as a result, the airflow is reinforced several times and the residual droplets are thus drawn off. In addition, during the operation of the pump, the airflow enables the flow-guiding body to move and alter the position, thereby the droplets at different positions can be drawn off.

The sputtering during pumping the solution is controllable. When the solution is pumped in from the through-hole of the substrate, the flow rate is high, which may result in sputtering. The flow-guiding body may stop the sputtering when the solution is pumped in. The stopper in the tank is provided to ensure that the flow-guiding body will not emerge from the liquid surface, reducing the non-contacting time between the flow-guiding body and the solution. The coating on the flow-guiding body has the simpler process and is more convenient to control the coating quality compared to the coating in the vessel.

The efficiency of the reaction is enhanced. The surface of the flow-guiding body is coated and the antibody is coated on the flow-guiding body, and then the flow-guiding body is placed in the sample vessel. After the sample is added, the antibody is binded to the antigen. The pump is operated in the sample tank such that the solution can flow ceaselessly between the two tanks. And the coated flow-guiding body rotates accordingly, making the antigen in the solution contact with the antibody coated on the surface of the flow-guiding body effectively, producing the effect much more sufficient than vibration, thereby increasing the efficiency of the reaction.

Figure 1:
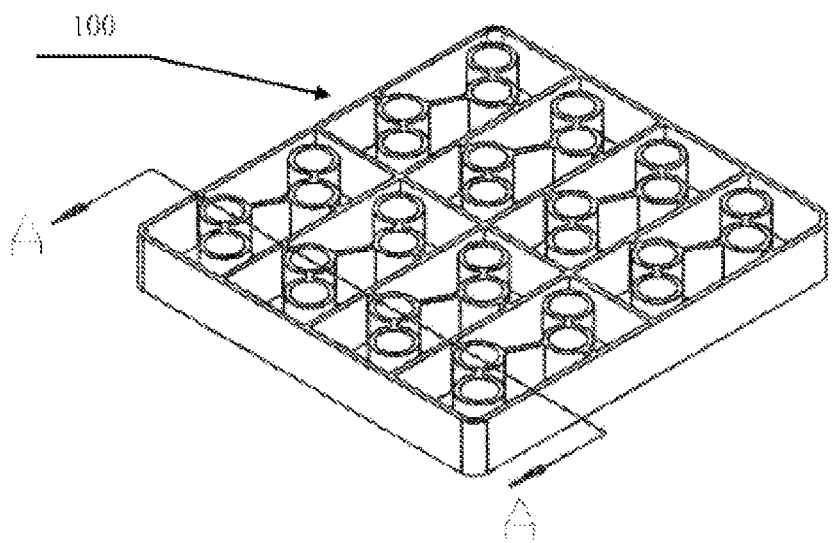
FIG. 1 is a schematic view of the structure of the polymeric microfluidic chip according to the present application.
Figure 2:
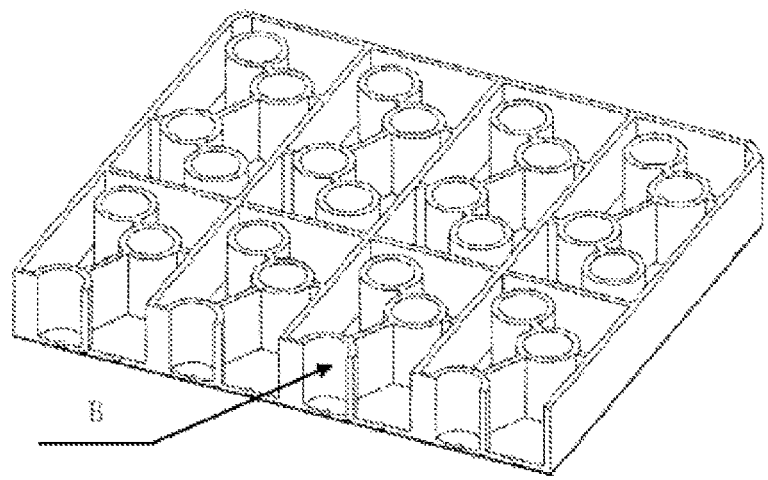
FIG. 2 is a cross-sectional view of the solution tank 101 along the direction of A-A in FIG. 1.
Figure 3:
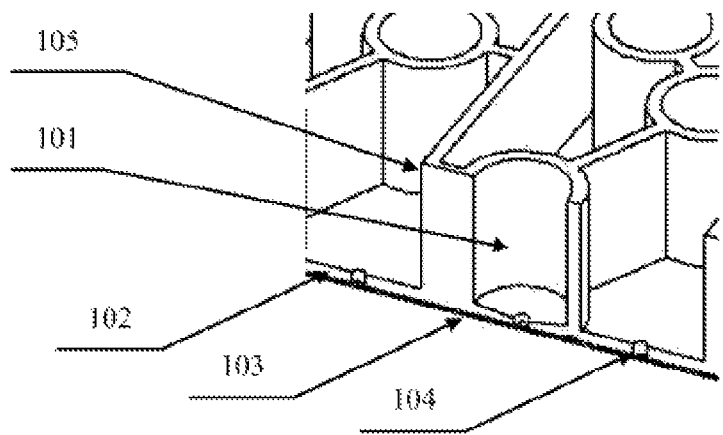
FIG. 3 is a partially enlarged view at the position B in FIG. 2.

The components represented by each reference number in FIGS. 1-14 are listed in table 1.

TABLE 1

| The components represented by each reference number | | |
|---|---|---|
| microfluidic-controlled chip (100) | | |
| solution tank (101) | substrate (102) | diaphragm (103) |
| substrate through-hole (104) | wall of the solution tank (105) | channel (106) |
| flow-guiding body (111) | junk ring (112) | solution (113) |
| residual droplet (114) | airflow (115) | |
| sample tank (201) | sample tank valve (211) | |
| dilution liquid tank (202) | dilution liquid tank valve (212) | sample dilution pump (302) |
| marking liquid tank (203) | marking liquid tank valve (213) | sample marking pump (303) |
| dissociation liquid tank (204) | dissociation liquid tank valve (214) | sample dissociation reinforce pump (304) |
| washing liquid tank (205) | washing liquid valve (215) | sample washing pump (305) |
| effluent liquid tank (206) | effluent liquid valve (215) main valve (217) | sample effluent pump (306) |
| sample-addition unit (401) | detection unit (402) | microfluidic control unit (403) |

DETAILED DESCRIPTION OF THE PREFERRED EMBODIMENTS

The following examples are only for the purpose of illustrating the present application, not limiting the scope of the present application.

The flow-guiding body in the examples may be regular sphere or irregular geometrical sphere. When the solution tank is of irregular shape, the flow-guiding body of irregular shape can be adopted. The flow-guiding body may be made of polymer or composite material combined by organics or inorganics, e.g. one of polyethylene, polystyrene, teflon, wood, silica gel or the composite thereof.

In the examples, the PMMA used is purchased from Continent Plymer Co. with the label of CP-51 and the ABS used is purchased from Dow Chemical Co. with the label of 340. The automatic sample-addition apparatus is purchased from Tecan Group Ltd.

The pharmaceuticals in the examples are analytically pure unless indicated otherwise. In the examples, all methods used are conventional methods in the art unless indicated otherwise.

Example 1

Preparation of Coated Flow-Guiding Sphere 1) the carcinoembryonic antibody to be coated is diluted with 50 mM pH 9.6 sodium carbonate-bicarbonate buffer liquid by 1:6000 for use;

2) the flow-guiding sphere is placed into the beaker and the diluted solution of carcinoembryonic antibody is added with the amount of 100 μl/per sphere;

3) the aforementioned beaker is sealed and placed on the shaking table at 4° C. with shaking for 20 hours;

4) the coating is finished and them washed twice with the washing liquid; the washing liquid is 10 mM pH 7.4 PBS (phosphate buffer liquid) containing 5% Tween-20 calculated according to 300 μl/per coated sphere;

5) after washed, the coated flow-guiding sphere is placed on the water absorption filter paper to sip up the remaining solution; and then placed into the beaker; an amount of the confining liquid is added based on the amount of 150 μl/per coated sphere, and then confined for 2 hours at room temperature; and the confining liquid is 10 mM pH 7.4 PBS containing 1% BSA;

6) after the confining is finished, the confining liquid is poured out, and the coated flow-guiding sphere is placed on the water absorption filter paper to sip up the remaining solution and then placed into the thermostatic incubator at 28° C. and dried for 20 hours.

Example 2

Silicification of the Flow-Guiding Body

The flow-guiding body is made of polyethylene. With the ethanol solution of 1% APES (aminopropyl triethoxysilane) as the silicide liquid, 500 mL silicide liquid is charged into the beaker of 1000 mL. The flow-guiding body is placed into the beaker and fully immersed. After Silicification for 1 min, the flow-guiding body is taken out from the beaker and standed in the air for 0-5 seconds. After 5 seconds, the flow-guiding body is placed into a beaker containing ultrapure water, immersed, shaking and then draining off the water. Afterwards, the flow-guiding body is placed into the beaker containing the ethanol, immersed, shaking and then draining off the ethanol. Thereafter, it is placed on the clean and dry gauze or filter paper. After part of the ethanol solution is volatilized, the flow-guiding body is flatwise put into oven at 40° C. and dried for 30 min.

Example 3

Irregular Flow-Guiding Body

Figure 7:
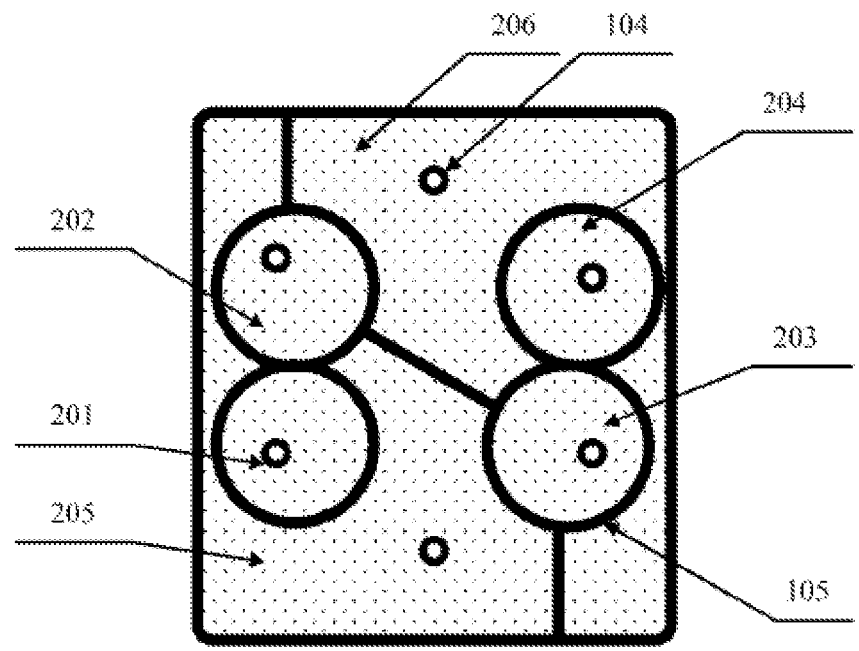
FIG. 7 is a top view of the solution tank in the polymeric microfluidic chip according to the present application.

The microfluidic chip is made of PMMA and includes six solution tanks, a sample tank 201, a dilution liquid tank 202, a marking liquid tank 203, a dissociation liquid tank 204, a washing liquid tank 205, an effluent liquid tank 206, referring to FIG. 7. The flow-guiding body placed within the effluent liquid tank is made of silica gel and has a same shape as that of the effluent liquid tank without being coated on the surface.

Example 4

Polymeric Microfluidic Chip with a Flow-Guiding Sphere

It shows six solution tanks, referring to FIG. 7: a sample tank 201, a dilution liquid tank 202, a marking liquid tank 203, a dissociation liquid tank 204, a washing liquid tank 205, an effluent liquid tank 206, and a wall 105 of the solution tank, and a substrate through-hole 104 is provided at the bottom of each tank.

Figure 8:
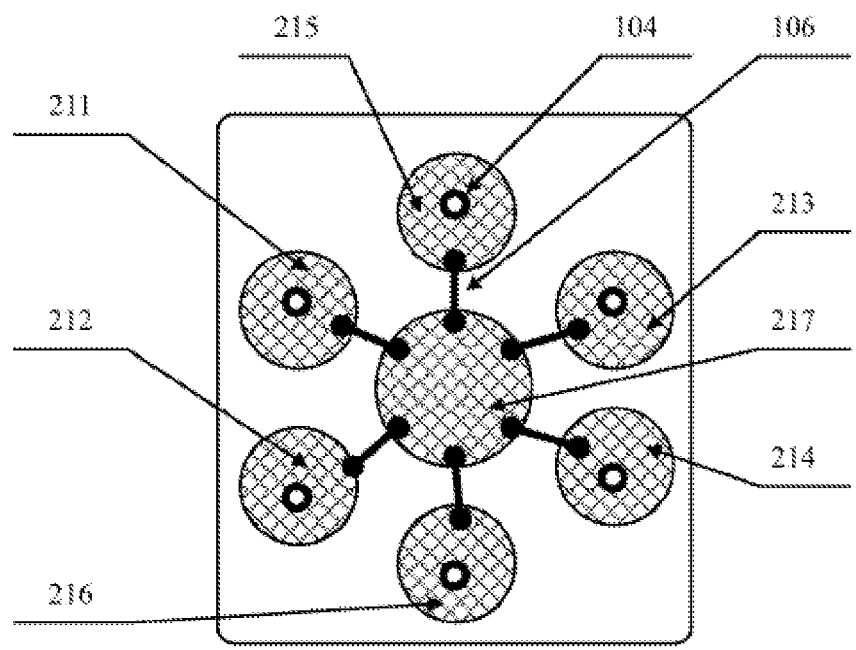
FIG. 8 is a bottom view of the polymeric microfluidic chip according to the present application.

It shows seven valves, referring to FIG. 8: sample tank valve 211, a dilution liquid tank valve 212, a marking liquid valve 213, a dissociation liquid tank valve 214, a washing liquid valve 215, an effluent liquid valve 216, a main valve 217, as well as channels 106 between the main valve and respective valves.

Figure 9:
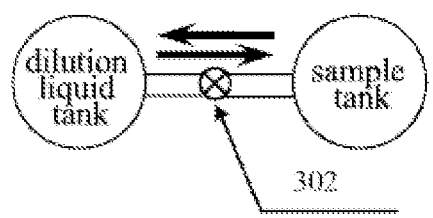
FIG. 9 is a view of the structure of the sample dilution pump 302.

Referring to FIG. 9, the sample tank valve 211, the main valve 217, the dilution liquid tank valve 212 and a substrate through-hole 104 as well as channels 106 constitute a two-way pump between the sample tank 201 and the dilution liquid tank 202, namely the sample dilution pump 302.

Figure 10:
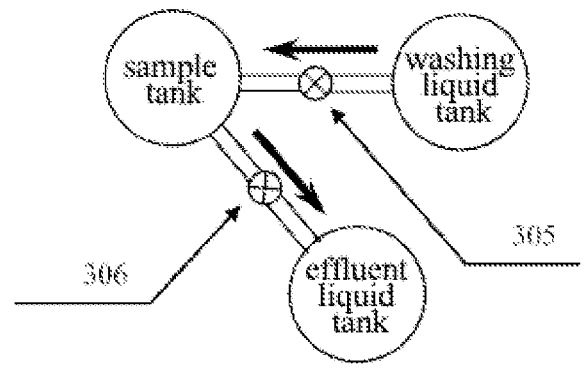
FIG. 10 are views of the structures of the sample washing pump 305 and the sample effluent liquid pump 306.
Figure 11:
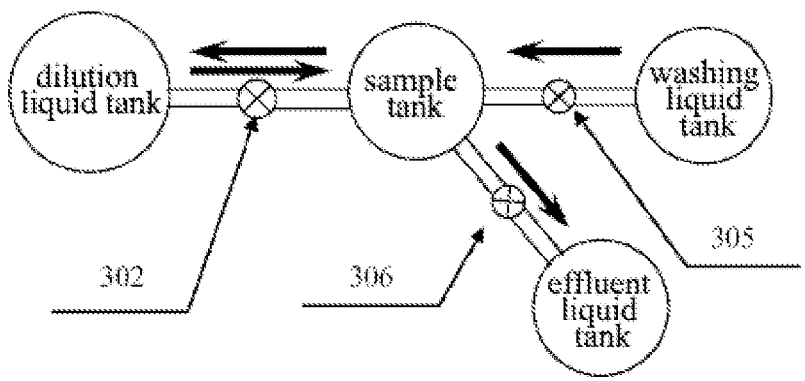
FIG. 11 is a view illustrating the connection of the dilution liquid tank, the sample tank and the washing liquid tank.

Referring to FIG. 10, the sample tank valve 211, the main valve 217, the washing liquid valve 215 and the through-hole as well as channel constitute the one-way pump between the sample tank 201 and the washing liquid tank 205, namely the sample washing pump 305; and the sample tank valve 211, the main valve 217, the effluent liquid valve 216 and the through-hole as well as channel constitute the one-way pump between the sample tank 201 and the effluent liquid tank 206, namely the sample effluent liquid pump 306.

Figure 12:
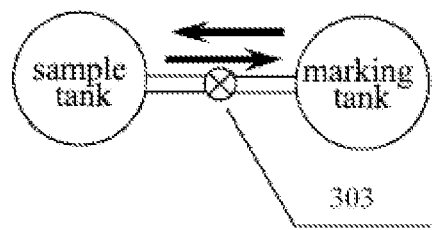
FIG. 12 is a view of the structure of the sample marking pump 303.

Referring to FIG. 12, the sample tank valve 211, the main valve 217, the marking liquid tank valve 213 and channel constitute the two-way pump between the sample tank 201 and the marking liquid tank 203, namely the sample marking pump 303.

Figure 13:
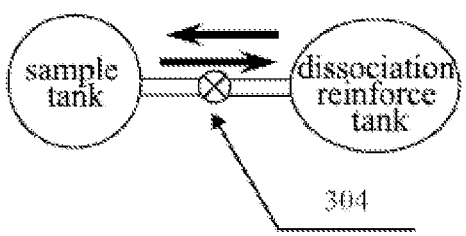
FIG. 13 is a view of the structure of the sample dissociation reinforce pump 304.
Figure 14:
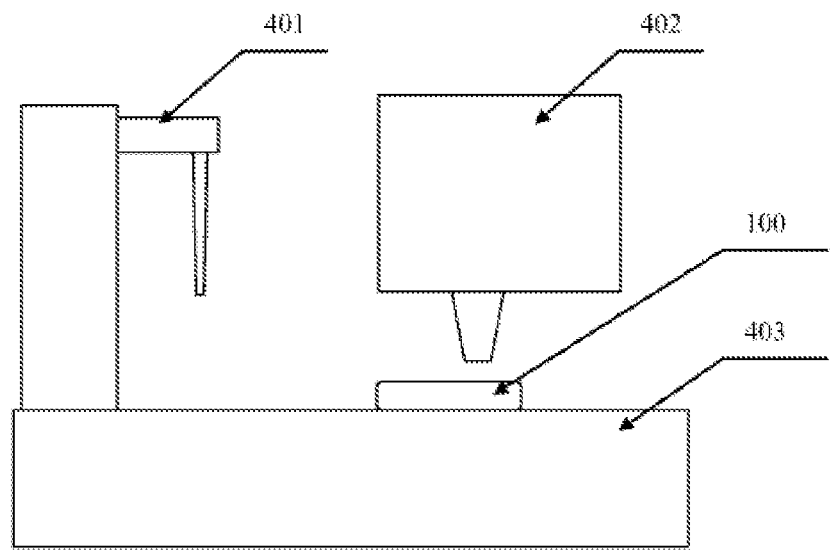
FIG. 14 is a schematic view of the detection device of the polymeric microfluidic chip according to the present application.

Referring to FIG. 13, the sample tank valve 211, the main valve 217, the dissociation liquid tank valve 214 and channel constitute the two-way pump between the sample tank 201 and the dissociation liquid tank 204, namely the sample dissociation reinforce pump 304.

Figure 4:
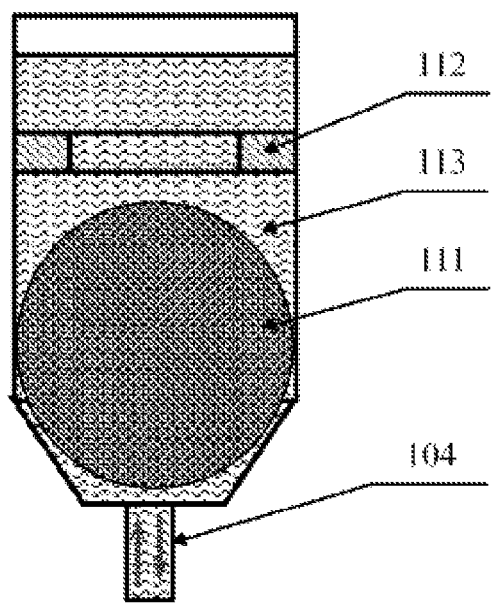
FIG. 4 is a cross-sectional view of the solution tank.
Figure 5:
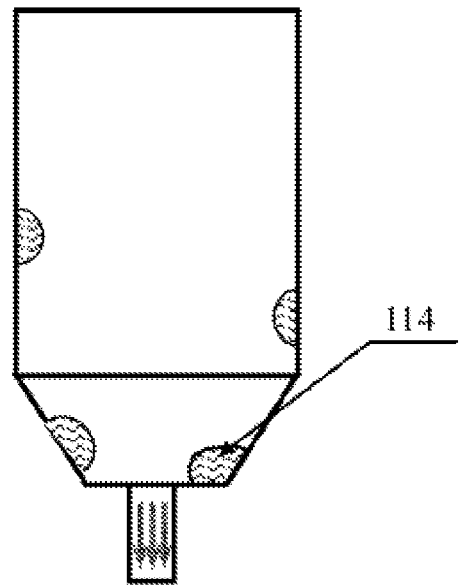
FIG. 5 is a cross-sectional view of the solution tank with residual droplet 114 when there is no flow-guiding body.
Figure 6:
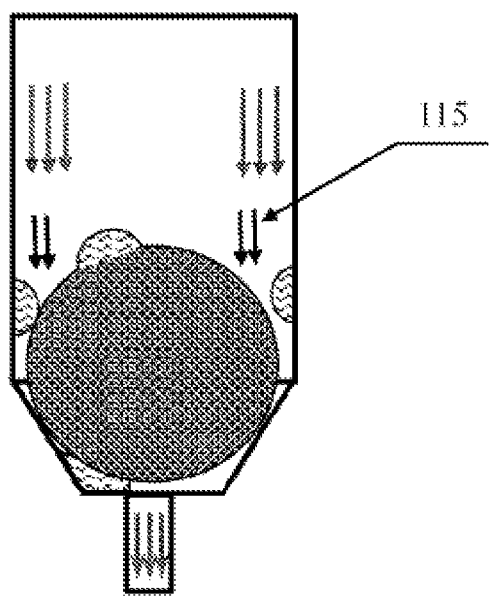
FIG. 6 is a cross-sectional view of the solution tank with airflow 115 generated by the discharge of the solution when there is a flow-guiding body.

Referring to FIGS. 4-6, the coated flow-guiding sphere 111 is placed within the sample tank 201. The diameter of the sample tank is 6.4 mm and the diameter of the coated flow-guiding sphere is 5.5 mm. The material of the sphere body is polystyrene. A stopper 112 in the shape of circular ring is disposed over the sample tank and fastened to the sample tank.

Example 5

Liquid Drainage Experiment for the Polymeric Microfluidic Chip with a Flow-Guiding Body Adopting the polymeric microfluidic chip of the example 4, a diameter of the cylinder vessel has a diameter of 6.4 mm and a depth of 10 mm, and the flow-guiding body in a shape of circular has a diameter of 5.5 mm (FIG. 6), it is made of polystyrene and contains solution of 200 μl. The maximum liquid volume pumped by the pump is 10 μl per time for 30 times. The experimental result is listed in table 2.

TABLE 2

The result of the Liquid Drainage Experiment of the microfluidic chip

| experiment | without the flow-guiding body | | with the flow-guiding body | |
| --- | --- | --- | --- | --- |
| | residual amount (μl) | residual rate | residual amount (μl) | residual rate |
| experiment 1 | 32.5 | 16.3% | 5.5 | 2.8% |
| experiment 2 | 30.0 | 15.0% | 5.0 | 2.5% |
| experiment 3 | 28.0 | 14.0% | 4.2 | 2.1% |
| average | 30.2 | 15.0% | 4.9 | 2.5% |

Example 6

Detection of Anti-Carcinoembryonic Antigen with Microfluidic Chip

1) Preparation of $Eu^{3+}$-DTPA: 1-(4-benzyl isothiocyanate) diethylenetriaminepenta-acetic acid (abbreviated as DTPA)

is diluted with purified water (containing $Eu^{3+}10^{-6}$ mol/L). The solution is placed into water bath at a constant temperature of 37° C. for heating reaction 2 h, to obtain a solution of europium chelator.

2) Anti-carcinoembryonic antigen monoclonal antibody is marked with $Eu^{3+}$DTPA: 1 mg of the anti-carcinoembryonic antigen monoclonal antibody is dialysed with 0.1M carbonate buffer liquid (pH 9.3) at 4° C. for 16 h. The antibody solution after dialysis is transferred to EP tube (plastic centrifuge tube). 0.2 mg of $Eu^{3+}$-DTPA is taken to add into the antibody solution and stirred for 14 h at room temperature in the dark.

3) Purification: The Superdex 200 filler is mixed well and charged into the 1×30 cm chromatography column. Upon the filler sinks, the column is compressed with purified water at a controlled flow rate of 2.5 ml/min and 2 column volumes will suffice. After the column is compressed, the column is treated with 0.1 mmol/L of NaOH at a controlled flow rate of 2.5 ml/min, and 2 column volumes will suffice. Afterwards, it can be washed level with water, then the purified column is equilibrated with the column equilibration solution (0.1% high-purity BSA bovine serum albumin water solution) for 1 h. The antibody marked in the step 2) is slowly added to the column by using the pipettor. The sample is eluted with the eluent (50 mM Tris-HCl tris hydroxymethyl aminomethane hydrochloride buffer liquid containing 0.9% NaCl and 0.05% sodium azide, pH 7.8) at a controlled flow rate of 1 ml/min.

4) Collection: The sample is collected in 1 ml/tube. According to the absorbance value at 280 nm of the protein detector, five tubes with high absorbance value is selected to combine, and the objective product is filtered through 0.22 μm filter membrane and sterilized, then placed in the environment of 4° C. for preservation, to obtain europium-marked carcinoembryonic antigen antibody solution, which is abbreviated as europium-marked solution.

5) Preparation of fluorescence enhancement liquid: 6 ml glacial acetic acid is adjusted with 0.1M potassium hydrogen phthalate to pH 3.2, added with 15 umol β-NTA (β-naphthoyl trifluoroacetone), 50 μmol TOPO (tri-n-octyl phosphine oxide), 1 ml Triton X-100 (polyethylene glycol octyl phenyl ether), and added with purified water to 1 L, and then mixed well.

6) Preparation of Sample Diluent: Tris-HCl buffer liquid containing 1% bovine serum albumin and 0.02% disodium ethylenediaminetetraacetic acid;

7) Preparation of washing solution: 0.2 MTris-HCl buffer liquid containing 5% Tween20 (Tween20);

8) Detection:

a) sample-addition and reagent-addition. 100 μl of the sample europium-marked carcinoembryonic antigen antibody solution prepared in step 4) is added to the sample tank 201 of the microfluidic detection chip 100 prepared in Example 4. The microfluidic detection chip 100 disposed on the microfluidic control unit 403, and the dilution liquid, washing liquid and fluorescence enhancement liquid are placed well;

b) initiating the detection. 300 μl dilution liquid is added into the dilution liquid tank 202, 2.0 ml washing liquid is added into the washing liquid tank 205, 200 μl europium-marked liquid is added into the marking liquid tank 203, and 150 μl fluorescence enhancement liquid is added into the dissociation liquid tank 204 by using the automatic sample-addition apparatus;

c) binding reaction of antigen and antibody (coated). The sample dilution pump 302 works bi-directionally, such that the samples in sample tank 201 and in the dilution liquid tank 202 are mixed with the dilution liquid for 30-60 min. When the mix stops, all mixed liquid is stored in the sample tank 201;

d) discharge of the effluent. The sample effluent pump 306 works unidirectionally, discharging the mixing liquid in the sample tank 201 into the effluent liquid tank 206;

e) washing. The sample washing pump 305 works unidirectionally, sucking the washing liquid into the sample tank 201. Then, the step d) is performed to discharge the effluent liquid. The step e) and step d) are performed repeatedly and washing is performed for 4 times.

f) europium marking. The sample marking pump 303 works bidirectionally such that the europium-marked liquid flows between the sample tank 201 and the marking liquid tank 203. The europium-marked liquid is mixed with "the antigen-antibody (coated) reaction combined body" obtained in the step c) for 30 min. When the mix stops, the marked liquid remains in the sample tank 201 and then the step d) is performed to discharge the effluent liquid into the effluent tank 206;

g) wash again, and step e) is performed for 5 times;

h) dissociation enhancement. The sample dissociation reinforce pump 304 works bidirectionally such that the dissociation reinforce liquid flows between the sample tank 201 and the dissociation liquid tank 204 to dissociate for 5 min. When the dissociation stops, the dissociation reinforce liquid is in the dissociation liquid tank 204;

i) detection. The detecting unit 402 is moved to the detecting location of microfluidic detecting chip 100 for detection, referring to FIG. 14.

The above examples are only description of the preferred embodiments of the present invention, but it does not limit the scope of the present invention. Various modifications and improvements made by those skilled in this art without departing from the concept and the spirit of the present invention are within the protection scope specified by the appended claims of the present application.

INDUSTRIAL APPLICABILITY

The micro-fluidic chip provided by the present invention is capable of reducing the residual of the discharge liquid, making that a gap is formed between the flow-guiding body and the vessel and the airflow is thus reinforced to draw off the residual droplet. The stopper is provided to ensure that the flow-guiding body will not emerge from the liquid surface, reducing the non-contacting time between the flow-guiding body and the solution. The coating on the flow-guiding body has a simpler process and is more convenient to control the quality of the coating compared to the coating in the vessel. The sputtering during the pumping of the solution is controllable so as to easily control the quality of the coating. The rotation of the flow-guiding body in the solution tank makes the antigen in the solution contact with the antibody coated on the surface of the flow-guiding body effectively, which has a more sufficient effect than vibration, thereby increasing the efficiency of the reaction.

The invention claimed is:

1. A microfluidic chip comprising:
at lease one solution tank of a microfluidic chip, the at least one solution tank defining an inner side wall surface; and
a flow-guiding body disposed in the at least one solution tank of the microfluidic chip, the flow-guiding body defining an outer surface spaced from the inner side wall surface to define a gap therein between, the gap between the outer surface of the flow-guiding body and the inner side wall surface of the solution tank depending on a viscosity of a solution in the solution tank, wherein if the viscosity of the solution is 0.6-1.2 mPa·s, the gap is 0-0.9 mm, and if the viscosity of the solution is 1.2-6.0 mPa·s, the gap is 0.9-1.5 mm.

2. The microfluidic chip of claim 1, wherein a shape of the flow-guiding body corresponds to a shape of the solution tank, and is one of a sphere, oblate spheroid, polyhedron or irregular geometry.

3. The microfluidic chip of claim 1, wherein the outer surface of the flow-guiding body is treated by silicification.

4. The microfluidic chip of claim 1, wherein the outer surface of the flow-guiding body is coated with an antigen or antibody.

5. The microfluidic chip of claim 1, further comprising a stopper disposed over the flow-guiding body and fastened to a wall of the solution tank.

6. The microfluidic chip of claim 1, at least one solution tank comprises a plurality of solution tanks comprising a sample tank having a sample through-hole at a bottom end thereof, a dilution liquid tank having a dilution liquid through-hole at a bottom end thereof, a marking liquid tank having a marking liquid through-hole at a bottom end thereof, a dissociation liquid tank having a dissociation liquid through-hole at a bottom end thereof, a washing liquid tank having a washing liquid through-hole at a bottom end thereof, and an effluent liquid tank having a effluent liquid through-hole at a bottom end thereof, and further comprising a sample tank valve connected to the sample tank, a dilution liquid tank valve connected to the dilution liquid tank, a marking liquid valve connected to the marking liquid tank, a dissociation liquid tank valve connected to the dissociation liquid tank, a washing liquid valve connected to the washing liquid tank, an effluent liquid valve connected to the effluent liquid tank; each valve connected to a main valve via channels;
the sample tank valve, the main valve, the dilution liquid tank valve as well as respective through-holes and channels constitute a two-way sample dilution pump between the sample tank and the dilution liquid tank;
the sample tank valve, the main valve, the washing liquid valve as well as respective through-holes and channels constitute a one-way sample washing pump between the sample tank and the washing liquid tank;
the sample tank valve, the main valve, the effluent liquid valve as well as respective through-holes and channels constitute a one-way sample effluent liquid pump between the sample tank and the effluent liquid tank;
the sample tank valve, the main valve, the marking liquid valve and respective channels constitute a two-way sample marking pump between the sample tank and the marking liquid tank; and
the sample tank valve, the main valve, the dissociation liquid tank valve and respective channels constitute a two-way sample dissociation reinforce pump between the sample tank and the dissociation reinforce liquid tank.

7. The microfluidic chip of claim 1, further comprising utilizing the microfluidic chip in biochemistry, immunology, or molecule detection.

8. A microfluidic chip comprising:
a plurality of solution tanks, each of the plurality of solution tanks comprising defining an inner side wall surface, the plurality of solution tanks comprising:
a sample tank having a sample through-hole at a bottom end thereof;
a dilution liquid tank having a dilution liquid through-hole at a bottom end thereof;
a marking liquid tank having a marking liquid through-hole at a bottom end thereof;
a dissociation liquid tank having a dissociation liquid through-hole at a bottom end thereof; and
a washing liquid tank having a washing liquid through-hole at a bottom end thereof;
a sample tank valve connected to the sample tank;
a dilution liquid tank valve connected to the dilution liquid tank;
a marking liquid valve connected to the marking liquid tank;
a dissociation liquid tank valve connected to the dissociation liquid tank;
a washing liquid valve connected to the washing liquid tank;
an effluent liquid valve connected to the effluent liquid tank;
a main valve connected to each of the sample, dilution liquid, marking liquid, dissociation liquid, washing liquid and effluent liquid valves via a plurality of channels; and
a plurality of flow-guiding bodies, each disposed in one of the plurality of solution tanks, each of the plurality of flow-guiding bodies defining an outer surface spaced from the inner side wall surface of the one of the plurality of solution tanks to define a gap of up to 1.5 mm;
wherein the sample tank valve, the main valve, the dilution liquid tank valve and respective through-holes and channels constitute a two-way sample dilution pump between the sample tank and the dilution liquid tank;
wherein the sample tank valve, the main valve, the washing liquid valve and respective through-holes and channels constitute a one-way sample washing pump between the sample tank and the washing liquid tank;
wherein the sample tank valve, the main valve, the effluent liquid valve and respective through-holes and channels constitute a one-way sample effluent liquid pump between the sample tank and the effluent liquid tank;
wherein the sample tank valve, the main valve, the marking liquid valve and respective channels constitute a two-way sample marking pump between the sample tank and the marking liquid tank; and
wherein the sample tank valve, the main valve, the dissociation liquid tank valve and respective channels constitute a two-way sample dissociation reinforce pump between the sample tank and the dissociation reinforce liquid tank.

9. The microfluidic chip of claim 8, wherein a shape of the flow-guiding body corresponds to a shape of the solution tank, and is one of a sphere, oblate spheroid, polyhedron or irregular geometry.

10. The microfluidic chip of claim 8, wherein the gap between the outer surface of the flow-guiding body and the inner side wall surface of the solution tank depending on a viscosity of a solution in the solution tank, wherein if the viscosity of the solution is 0.6-1.2 mPa·s, the gap is 0-0.9 mm, and if the viscosity of the solution is 1.2-6.0 mPa·s, the gap is 0.9-1.5 mm.

11. The microfluidic chip of claim 8, wherein the outer surface of the flow-guiding body is treated by silicification.

12. The microfluidic chip of claim 8, wherein an antigen or antibody is coated on a surface of the flow-guiding body.

13. The microfluidic chip of claim 8, further comprising a stopper disposed over the flow-guiding body and fastened to a wall of the solution tank.

14. The microfluidic chip of claim 8, further comprising utilizing the microfluidic chip in biochemistry, immunology, or molecule detection.

* * * * *